United States Patent [19]

Crawford et al.

[11] Patent Number: 4,614,729

[45] Date of Patent: Sep. 30, 1986

[54] SUPPORTED ORGANOMETALLIC COMPOUNDS FOR UTILIZATION IN PURIFICATION OF FLUIDS

[75] Inventors: Janet E. Crawford, No. White Plains; Ronald A. Epstein, Yonkers, both of N.Y.; Kelly B. Triplett, Stamford, Conn.

[73] Assignee: Stauffer Chemical Company, Westport, Conn.

[21] Appl. No.: 665,239

[22] Filed: Oct. 26, 1984

[51] Int. Cl.⁴ .......................... B01J 31/12; B01J 31/14
[52] U.S. Cl. ..................................... 502/401; 502/103; 502/120; 502/132; 502/152; 502/154; 585/830; 210/679
[58] Field of Search ............... 502/154, 401, 152, 103, 502/120, 132

[56] References Cited

U.S. PATENT DOCUMENTS

| | | | |
|---|---|---|---|
| 3,202,645 | 8/1965 | Yancey | 502/114 X |
| 3,274,120 | 9/1966 | Aftandilian | 502/152 |
| 3,620,981 | 11/1971 | Magoon et al. | 502/117 |
| 3,840,511 | 10/1974 | Ballard et al. | 502/154 X |
| 4,056,669 | 11/1977 | Ballard et al. | 502/154 X |
| 4,263,171 | 4/1981 | Shida et al. | 502/104 |
| 4,333,851 | 6/1982 | Speakman et al. | 502/113 |
| 4,397,762 | 8/1983 | Johnstone | 502/113 |
| 4,435,520 | 3/1984 | Aylward | 502/107 |

FOREIGN PATENT DOCUMENTS 1462762 11/1966 France .

OTHER PUBLICATIONS

Sato et al, J. Catalysis, vol. 7 (1967), pp. 342–351.
Ballard et al, European Plastics & Rubber Conference, Paris (1978), Part A-4, pp. 1–7.
Webster's Seventh New Collegiate Dictionary, Pub. by G & C Merriam Co., Springfield, Mass. (1967), p. 364.

*Primary Examiner*—Patrick P. Garvin
*Attorney, Agent, or Firm*—Vivienne T. White

[57] ABSTRACT

Supported organometallic compounds of Groups II, III and IV of the Periodic Table are utilized for purifying fluids particularly hydrocarbon fluids, noble gases, nitrogen and hydrogen and desirable hydrocarbon solvents and olefins to remove impurities such as oxygen, sulfur, halogen-containing compounds, active hydrogen compounds and other polar compounds. The supported organometallic compounds, preferably supported metal alkyls, are prepared by reacting the pretreated dried solid support material with the organometallic compounds in such a manner as to effect loading or impregnation of the organometallic moieties onto the support.

37 Claims, 4 Drawing Figures

SUPPORTED ORGANOMETALLIC COMPOUNDS FOR UTILIZATION IN PURIFICATION OF FLUIDS

BACKGROUND OF THE INVENTION

1. Field of the Invention

The invention pertains to compositions comprising inorganic oxide-supported organometallic compounds of Groups II, III and IV of the Periodic Table, their preparation and their use in the purification of fluids, such as hydrocarbons and particularly the purification of solvents and olefins.

2. Related Art

Billions of pounds of ethylene, propylene and 1-butene are polymerized each year in the United States. The primary products are low-density polyethylene (LDPE), linear low-density polyethylene, high-density polyethylene and polypropylene. While the production processes vary widely, all polymerization processes use sophisticated catalyst systems that are vulnerable to poisoning by various impurities. Polyolefin producers, therefore, usually employ elaborate and expensive processes to remove the undesirable impurities, not only from the olefin monomers but also from the process solvents and nitrogen gas used for blanketing the system.

There is a strong trend toward the use of advanced catalysts which produce so much polymer per pound of catalyst that the producer does not have to de-ash the crude polymer to remove any catalyst residue. Such a change affords a substantial increase in yield and a simultaneous reduction in operating costs. It also reduces the capital cost of a new plant significantly. These new super-active catalysts are much more susceptible to poisoning than their predecessors.

The major catalyst poisons are reactive impurities (e.g., $CO_2$, CO, COS, $H_2O$, $H_2S$, $O_2$, and acetylenics) in the olefin monomers. Although extensive purification is being done in most plants, current technology is usually not adequate to achieve the more stringent purity specifications necessary to realize the full benefits of the advanced catalysts. As the quantity of polymer produced from each pound of catalysts is increased, e.g., five- to ten-fold, the amount of feedstock impurities that can be tolerated decreases correspondingly. Total reactive impurities may have to be reduced to one hundred parts per billion or less. Further, current purification processes do not always afford adequate protection against upsets caused by "spikes" of impurities in the monomer, regardless of the purification system being used.

It is known in the prior art to purify olefins by various processes usually entailing treating the olefin with absorbents such as silica gel or ignited aluminum oxide, diethyl zinc, or with a solution containing triethyl aluminum, tripropyl aluminum, triisobutyl aluminum, trimethyl aluminum, triphenyl aluminum, etc.

U.S. Pat. No. 3,202,645 discloses a surface treated inorganic, solid polymerization catalyst wherein the catalyst comprises a reaction product of a compound of a metal chosen from Groups IIb to IIIb of the Periodic Table the hydroxyl groups on the surface of a finely divided particulate inorganic solid and a halide-type compound of Groups IVa, V, VIa, VIIa or period 4 of a Group VIII metal. The finely divided particulate material of the reference is said to be less than about 1 micron and preferably less than about 0.1 micron. The reference, therefore, is directed to the use of extremely fine powders. The reaction product of the reference is then combined with a transition metal halide for use in polymerization processes.

U.S. Pat. No. 3,274,120 discloses a catalyst composition having increased hydroxyl groups bound thereto and the method of producing the composition. The composition and method taught comprises the use of a finely divided solid support material. The particle size of the support disclosed describes a fine powdery material.

U.S. Pat. No. 3,620,981 discloses a heterogenous catalyst composition comprising a hydrocarbon complex of certain transition metal halides supported on an acidic inorganic oxide catalyst support, which support is optionally pretreated with an alkyl aluminum compound prior to incorporation of the transition metal halide. The alkyl aluminum compounds generically (and apparanently incorrectly) represented by $R''_pAlX_{(31y)}$, where $R''$ is an alkyl of up to 8 carbon atoms; X is a halogen and y is a whole number from one to three. Compounds listed include triethyl and triisobutyl aluminum. From the examples provided it can be concluded that the inorganic oxide support material is a powder.

An article appearing in the Journal of Catalysis, Vol. 7, pages 342 to 351 (1967) entitled "Hydroxyl Groups on Silica, Alumina, and Silica-Alumina Catalysts" by Sato et al. describes experimental methods used to characterize the surface hydroxyls on silica, alumina, and silica-alumina solids. In the experiments therein, which were carried out in a closed system under normal nitrogen atmosphere, the volume of alkane produced from the reaction of a metal alkyl with the surface hydroxyls was measured. In the experiments, the alumina was prepared by hydrolysis of redistilled aluminum isopropoxide in isopropyl alcohol with distilled water, was washed, filtered, dried at 120° C. and then calcined at 500° C. for 2 hours (see page 343). The procedure as described on page 344 comprised calcining about 0.2 gram of a catalyst at 450° C. in a reactor which is slowly heated under a nitrogen atmosphere then evacuated to $10^{-2}$ to $10^{-3}$ mm Hg for 2 hours, then cooled to room temperature and brought back to atmospheric pressure with nitrogen. Then 1.0 to 1.5 mls of the organometallic compound, e.g., triethyl aluminum, which comprised about four or five equivalents of the organometallic compound to the one of surface hydroxyl groups, was poured into the reactor and the volume of the evolved gas was measured to determine the number of surface hydroxyl groups. It is apparent from the above description that the alumina utilized in the system was powdered alumina since there is no indication that the alumina produced by the process disclosed above was shaped. The solvent utilized in the process was decalin which is a very high boiling point solvent not suitable for use in a commercial process of purifying hydrocarbons since the decalin would remain in the system and be carried over during the purification process. Further, the process described in Sato utilizes a four to five fold excess of triethyl aluminum to hydroxyl groups whereas the instant process uses about a two fold excess of organometallic to metal oxide. As a result of the above, the material which would have been prepared by the process disclosed by Sato would not be useful as a purification media for liquids or gaseous feed streams.

A paper entitled "Lanthanide Catalysts for the Polymerization of Olefins" by Ballard et al. appearing in European Plastics and Rubbers Conference, 5th, Paris, 1978, part A-4, pages 1-7, briefly discloses on page 3 thereof, line 2, "ethylene gas (purified by BTS catalyst, molecular sieve and AlEt$_3$/Al$_2$O$_3$) . . . ". The paper utterly fails to elucidate what is meant by the ambiguous abbreviation "AlEt$_3$/Al$_2$O$_3$". The indication is that ethylene gas is purified by this system. There is no further disclosure relative to the purification of ethylene or any other olefin and more importantly, there is no reference, teaching or suggestion for purifying liquid feed streams.

French Pat. No. 1,462,762 describes the purification of propylene with a liquid aluminum alkyl. Gaseous propylene in the process is purified by a countercurrent system of liquid tripropyl aluminum. Countercurrent contact with a liquid aluminum alkyl is not a commercially useful process, however, because there will be significant entrainment of aluminum alkyl in the gas stream. This could cause deleterious effects downstream.

None of the cited art disclosed a purifying agent comprised of a granular metal oxide-supported organometallic compound prepared by either utilizing a granular inorganic oxide starting material or by utilizing a powder which is shaped after preparation.

SUMMARY OF THE INVENTION

It has now been discovered that supported organometallic compounds of Groups II, III and IV of the Periodic Table (hereinafter "organometallic compounds"), prepared as disclosed, are capable of purifying fluids such as hydrocarbon fluids in general and particularly solvents, noble gases, nitrogen, hydrogen and olefins. The preparation comprises reacting a pretreated granular support material with at least one organometallic compound generally in the presence of a solvent and then recovering the product therefrom. Contacting the hydrocarbon or other material with a sufficient amount of the supported organometallic compound for a sufficient time results in the removal of impurities.

DETAILED DESCRIPTION OF THE INVENTION

The invention is directed to the preparation of supported organometallic compounds, and to their use as a purifying agent for fluids such as hydrocarbon fluids and in particular for hydrocarbon solvents, noble gases, nitrogen, hydrogen and olefins. The term "hydrocarbon fluid" as used herein is defined to be a material which is a fluid at ambient temperatures or can be made fluid by heating or other means without decomposing the material. The hydrocarbon fluids can therefore be liquids, fluids derived from solids or gases and generally are $C_1$-$C_{30}$ alkanes; $C_2$-$C_{30}$ alkenes; $C_4$-$C_{10}$ dienes and to some extent oxygenated hydrocarbons which do not contain an active hydrogen. The purifying agent of the present invention would remove from the oxygenated hydrocarbons materials which are more reactive than the oxygenated hydrocarbon itself. Oxygenated hydrocarbons, for instance, such as esters, particularly methacrylate monomers and ketones are exemplary.

The preparation of the purifying agent comprises a reaction of the support material with the organometallic compound either neat or dissolved in a solvent and the recovery of the supported organometallic compound therefrom.

Impurities such as acetylene, methyl acetylene, allene, carbon dioxide, carbonyl sulfide, water, hydrogen sulfide, alkyl halides, alcohols and acids can be removed by treatment with the supported organometallic agent produced as disclosed herein. Improved polymerization activity of about 30% in a magnesium halide-supported titanium-containing polypropylene catalyst was obtained when tested at 90 psig (721.8 kPa).

Various materials can constitute the solid support material for use in preparing the purification agent. In general, metal oxides containing hydroxyl groups wherein the metals are from Groups II to IV of the Periodic Table can be utilized in the process of the invention. Particularly suitable metal oxides containing hydroxyl groups for practicing this invention are as for instance: alumina, silica, titania, magnesia or mixtures thereof.

A preferred material for use in practicing the invention is alumina.

The support material, e.g., alumina, for use in purifying applications is preferably in the form of shaped particles or granules so that the final product can be packed in a fixed bed. For applications where the feed stream is under pressure, a fixed bed packed with shaped particles or granules will give a much lower pressure drop across the packed bed than if the bed was packed with a powder. For commercial applications, a significant pressure drop across a purification bed would be detrimental as the feed stream would then have to be compressed back to its initial pressure for use in the final process. However, if the feed stream is not under pressure, for example with liquid hydrocarbons, the purification bed could be packed with the product in a powder form. In this case, the feed stream could be purified either by one pass through the bed or by recirculating the feed stream through the bed a number of times.

Generally, the hydroxyl ion-containing metal oxides prepared as disclosed herein are granular shaped particles. In the practice of the invention the preferred support material for use as a purification agent should have the following physical characteristics: particle size from about 0.04 cm (0.016 inch) and generally but not limited to about 1.3 cm (0.5 inch), preferred range being from about 0.16 cm (1/16 inch) to about 0.64 cm (174 inch); surface areas of from about 10 m$^2$/g to about 1000 m$^2$/g with from about 150 m$^2$/g to about 400 m$^2$/g being preferred; pore volume of from about 0.1 cm$^3$/g to about 7.0 cm$^3$/g with a preferred range of from about 0.3 cm$^3$/g to about 1 cm$^3$/g based on nitrogen BET (Brunauer, Emmett, and Teller) method.

The hydroxyl ion-containing metal oxide is reacted in the process of the invention with an organometallic compound. Prior thereto, the hydroxyl ion-containing metal oxide is pretreated by calcining prior to use to remove surface adsorbed water. The calcining temperature will depend on the specific metal oxide being utilized. Temperatures of from about 150° C. to about 800° C. are generally suitable for the metal oxides specified for use in the process of the invention. Alumina for instance can be calcined at temperatures of from about 300° C. to about 600° C. prior to being used in the preparation of the purifying agent.

Generally in the practice of preparing the supported organometallic compound of the invention, the organometallic compound is mixed with a solvent. The solvent utilized should of course be compatible with the specific organometallic compound being utilized, and it is advantageous to have a low boiling point generally of not greater than about 150° C. since high boiling solvents may remain in the pores of the supported organometallic compound and contaminate the materials being purified. Further, the solvent utilized should be inert to the organometallic compound being utilized and should preferably be a saturated or aromatic hydrocarbon. Solvents, such as n-pentane, n-heptane, n-hexane, benzene, toluene, n-octane, cyclohexane, xylene, and branched hydrocarbons, have been found suitable for use in the practice of the invention. Heptane has been found most suitable for use in the process of the invention.

The concentration of the organometallic compound when used with a solvent can range from about 1% to about 99%, but, for commercial convenience, should be from about 10% to about 30%.

Various organometallic compounds can be utilized in preparing the purifying agent. In general, organometallics from Groups II, III and IV of the Periodic Table can be utilized. Particularly suitable organometallic compounds are those known as metal alkyls, for instance aluminum alkyls. Preferred materials for use in practicing the invention are aluminum alkyls where the alkyl ranges from $C_1$ to about $C_8$.

The reaction of the hydroxyl-ion containing metal oxide and the metal alkyl compound results in the evolution of hydrocarbon gas. The proportion of the organometallic compound to the support material is not critical except for the necessity of reacting with the surface hydroxyl groups of the support material. The usual molar ratio of organometallic compound to support should be in the range of from about 0.05:1 to about 5:1 and preferably about 0.2:1 to 0.5:1. However, so long as the stoichiometric reaction amount is satisfied excess amounts of the organometallic compound is not detrimental and may be beneficial.

The organometallic compounds are readily handleable as a solution in inert solvents such as liquid or liquified hydrocarbons.

Various techniques of contacting the organometallic compound with the hydroxyl containing metal oxide can be employed. Following are illustrations of the various techniques of the reaction. In all instances, the hydroxyl-ion containing metal oxide in the form of either a powder but, preferably, generally shaped particles, such as formed pellets or spheres or granules is pretreated to remove surface water, generally by calcining prior to reacting with the organometallic compound. It may be possible to commercially obtain precalcined metal oxide, or metal oxide wherein surface water is removed, in which case it would not be necessary to pretreat prior to use to remove surface water. Purifying agents in the form of powders used to purify the various materials described are within the scope of the invention. The terms "shaped particles", "formed pellets", "spheres", and "granular" are used herein interchangeably and exclude powder. A desirable method comprises, for instance, transferring the calcined oxide material to a pressure equalizing addition column to which is added the organometallic compound in an inert solvent. The system is allowed to stand for a period of time necessary to complete the reaction with the hydroxyl ions on the surface of the oxide material and thereafter the solvent is drained from the column. In some operations the purification product may be used neat. The product comprising, for example, the aluminum alkyl carried on the oxide, however, is preferably washed once, and, desirably three times, with the solvent prior to preferably drying the product. Other variations of the above are as follows:

1. The process wherein the calcining oxide is transferred to a pressure equalizing addition column to which is added a solvent which is then drained from the system after being allowed to stand for a period of time necessary to wet the oxide. To the wet oxide is then added the organometallic compound in a solvent which is allowed to stand for a period of time necessary to complete the reaction with the surface hydroxyl ions of the oxide. As in the previous process, the product is then preferably washed and dried as indicated.
2. In this process variation, the calcined oxide is transferred to a reaction vessel containing stirring means. To the oxide is added a solvent with stirring. To the stirred system is added the organometallic compound in a solvent and the system is stirred for a period of time necessary to complete the reaction with the hydroxyl ions. Again as in the previous variations, the product is preferably washed and dried as indicated.
3. The organometallic compound in a solvent is added to a pressure equalizing addition funnel and to this solution is gradually added the calcined oxide. The system is allowed to stand for a period of time necessary to complete the reaction with the surface hydroxyl ions. As in the previous variations the product is preferably washed and dried as indicated.

The temperature of the reaction is usually about 20° C. and is lower than temperatures at which substantial thermal decomposition of the specific organometallic compound occurs. Broadly, temperatures within the range of about 0° C. to about 150° C. can be used, preferably about 15° C. to about 40° C. or about ambient temperature.

The reaction is effected in an inert gaseous atmosphere or in an environment which is filled with inert liquid. The time of contacting for the reaction purposes is that necessary to react with the surface hydroxyl groups to form the reactive species. Preferably, contact times of from about 0.5 to about 2 hours are acceptable although longer contact times are not detrimental. Usually the rate of interaction of, for instance, trialkyl aluminum compounds and metal oxides are high at room or elevated temperatures so that reaction periods within the above-defined ranges can be conveniently employed.

As is obvious from the previous discussion the product can be prepared with or without stirring during the reaction process. One desirable commercial method for preparing the purifying agent, as for instance, trialkyl aluminum on alumina or more specifically triethyl aluminum on alumina, previously described above, involves pretreating by calcining the metal oxide at a temperature of from about 300° C. to about 600° C. prior to transferring the calcined oxide into a column, and to this is added the solvent, allowing the system to stand for a period of time necessary to completely wet the oxide, draining prior to adding to the wet oxide a solution of the trialkyl aluminum in solvent, and then allowing the reactants to stand for a period of time necessary to react with the surface hydroxyl ion from the oxide. It is possible to reverse the order of addition of calcined alumina and solvent. The product formed is washed (e.g., three times) with a solvent and thereafter drained. The resulting wet product is then dried under vacuum.

The product morphology obtained is similar to the morphology of the metal oxide support used in the process.

The reaction, for example, of the triethyl aluminum with alumina ("TEAL on alumina") generates ethane and produces what is believed to be a surface bound diethyl aluminum species exemplified (in schematic form) by the following reaction:

where $Al_s$ is surface aluminum. The term "TEAL on alumina" may, therefore, be a misnomer, the reality being diethylaluminum bonded to alumina through an oxygen atom. The same reasoning would hold for other organometallics on the support.

Typically, the range of metal alkyl to alumina support is 0.0005 mole: 1 gram to 0.05 mole: 1 gram and preferably 0.0024 mole: 1 gram.

Generally, loadings of the organometallic compounds are in the range of from about 3.0 mole % to about 20.0 mole %. The extent of loading achieved will be dependent upon the specific organometallic compound utilized. For instance the "alkane loading" for trimethyl aluminum on alumina was found to range from about 2.0 to about 5.0 wt. % methane generated upon hydrolysis of the final product, whereas the loading for triethyl aluminum on alumina ranged from about 2.0 to about 10.0 wt. % ethane generated upon hydrolysis of the final product. By "alkane loading" is meant the amount of alkyl capable on the supported organometallic compound.

The prepared samples were analyzed for metal alkyl loading as measured by the amount of alkane evolved upon hydrolysis according to the following equation:

where R is a $C_1$ to $C_8$ alkyl group. Note that two moles of alkane are generated per one mole of metal alkyl originally reacted.

Analysis was carried out using a gas chromatography method referenced below. The data obtained is reported in Tables I, II, III and IV as weight percent alkane which is related to the amount of metal alkyl compound reacted with the support material as shown in the following equation where R is a $C_1$–$C_8$ alkyl group.

Determining loading of the organometallic compound stored under nitrogen was conducted in accordance with that disclosed by B. J. Philipp, W. L. Mudry, and S. C. Watson in Analytical Chemistry, Vol. 45, page 2298 (1973) which is incorporated herein by reference. Modification of that test method was made to accommodate the fact that the tested material was solid instead of a liquid as described in the process. In the method approximately 0.2 gram of the solid purifying agent was utilized to determine the extent of loading of the organometallic compound on the support material.

The following Examples are more descriptive embodiments of the method of preparation in accordance with the present invention. The preferred aluminas in general and the aluminas used in the examples were Rhone Poulenc's brand SCM 250A and Kaiser brand A201 except where noted.

EXAMPLE 1

The following materials were utilized in the preparation of the purifying agent as detailed:
20 g of alumina, formed into spheres;
30 ml of triethyl aluminum (TEAL) in heptane (25 wt. %) solution; and
150 ml of heptane distilled over calcium hydride and stored under nitrogen.

The alumina was first calcined in a flow of nitrogen at 400° C. for 24 hours and after calcination was stored under an inert atmosphere, nitrogen, until used. All preparations and handling were carried out under a nitrogen atmosphere at room temperature. The calcined alumina was transferred to a pressure equalizing addition funnel (a column) and to this alumina was added 30 ml. of the TEAL in heptane solution. The system was allowed to stand for 1 hour after which the remaining TEAL in heptane solution was drained from the column. A 50 ml amount of heptane was then added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 5.1 to 6.0 wt.% ethane were obtained.

EXAMPLE 2

The following materials were utilized in the preparation of the purifying agent as detailed:
20 g of alumina, formed into spheres;
30 ml of triethyl aluminum (TEAL) in heptane (25 wt. %) solution; and
200 ml of heptane distilled over calcium hydride and stored under nitrogen The alumina was first calcined in a flow of nitrogen at 400° C. for 24 hours and then stored under an inert atmosphere, nitrogen, until used. All preparations and handling were carried out under a nitrogen atmosphere at room temperature. The calcined alumina was transferred into a pressure equalizing addition funnel (a column) and to this alumina was added 50 ml of heptane. The system was allowed to stand for 30 minutes, and the heptane was then drained. To the wet alumina was added 30 ml of the TEAL in heptane solution, and the system was allowed to stand for one hour after which time the remaining TEAL in heptane solution was drained from the column. A 50 ml amount of heptane was then added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 4.3 to 5.2 wt. % ethane were obtained.

EXAMPLE 3

The following materials were utilized in the preparation of the purifying agent as detailed:
20 g of alumina, formed into spheres;
30 ml of triethyl aluminum (TEAL) in heptane (25 wt. %) solution; and
200 ml of heptane distilled over calcium hydride and stored under nitrogen.

The alumina was first calcined in a flow of nitrogen, at 400° C. for 24 hours and then stored under an inert atmosphere, nitrogen, until used. All preparations and handling were carried out under a nitrogen atmosphere at room temperature. The calcined alumina was transferred into a 3 necked round bottom flask equipped with a means of stirring. To the alumina was added 50 ml of heptane, and the alumina/heptane mixture was stirred. To this was added 30 ml of TEAL in heptane solution, and the system was stirred for four hours. After four hours the remaining TEAL in heptane solution was decanted, and then a 50 ml portion of heptane was added, and the system was stirred for 10 minutes. This heptane was then decanted and a fresh 50 ml portion of heptane added, followed by stirring for 10 minutes and decanting off the heptane. A final 50 ml portion of heptane was added, the system was stirred for 10 minutes and then the heptane was decanted. This resulting wet material was then dried under vacuum at room temperature. Loadings of 4.2 to 6.7 wt. % ethane were obtained.

EXAMPLE 4

The following materials were utilized in the preparation of the purifying agent as detailed:
20 g of alumina, formed into spheres;
30 ml triethyl aluminum (TEAL) in heptane (25 wt. %) solution; and
150 ml heptane distilled over calcium hydride and stored under nitrogen.

The alumina was first calcined in a flow of nitrogen at 400° C. for 24 hours and then stored under an inert atmosphere, nitrogen, until used. All preparations and handling were carried out under nitrogen atmosphere at room temperature. The 30 ml of TEAL in heptane solution was added to a pressure equalizing addition funnel (a column) and to this solution was gradually added the 20 g of alumina. The system was allowed to stand for 1 hour, after which the remaining TEAL in heptane was drained. 50 ml of heptane was then added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 3.0 to 4.7 wt. % ethane were obtained.

EXAMPLE 5

The following materials were utilized in the preparation of the purifying agent as detailed:
20 g of alumina formed into spheres;
35 ml of trimethyl aluminum (TMAL) in heptane (15.0 wt.%) solution; and
200 ml heptane distilled over calcium hydride and stored under nitrogen.

The alumina was first calcined in a flow of nitrogen at 400° C. for 24 hours and then stored under an inert atmosphere nitrogen, until used. All preparations and handling were carried out under a nitrogen atmosphere at room temperature. The calcined alumina was transferred into a 3 necked bottom flask equipped with a means of stirring. To the alumina was added 50 ml of heptane, and the alumina/heptane mixture was stirred. To this was added 35 ml of TMAL in heptane solution, and the system was stirred for four hours. After four hours the remaining TMAL in heptane solution was decanted and then a 50 ml portion of heptane was added and the system was stirred for 10 minutes. This heptane was then decanted and a fresh 50 ml portion of heptane added, followed by stirring for 10 minutes and decanting off the heptane. A final 50 ml portion of heptane was added, the system was stirred for 10 minutes and then the heptane was decanted. The resulting wet material was then dried under vacuum at room temperature. Loadings of 2.7 to 3.1 wt. % methane were obtained.

EXAMPLE 6

The following materials were utilized in the preparation of the purifying agent:
20 g alumina formed into spheres;
35 ml of trimethyl aluminum (TMAL) in heptane (15.0 wt. %) solution; and
150 ml heptane distilled over calcium hydride and stored under nitrogen.

The alumina was first calcined in a flow of nitrogen at 400° C. for 24 hours and, after calcination, stored under an inert atmosphere, nitrogen, until used. All preparations and handling were carried out under a nitrogen atmosphere at room temperature. The calcined alumina was transferred to a pressure equalizing addition funnel (a column) and to this was added 35 ml of the TMAL in heptane solution. The system was allowed to stand for 1 hour after which the remaining TMAL in heptane solution was drained from the column. Then 50 ml of heptane was then added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 3.8 to 3.9 wt. % methane were obtained.

EXAMPLE 7

The following materials were utilized in the preparation of the purifying agent:
20 g of alumina, formed into spheres;

56 ml of triisobutyl aluminum (TIBAL) in heptane (25 wt. %) solution; and 150 ml of heptane distilled over calcium hydride and stored under nitrogen.

The alumina was first calcined in a flow of nitrogen at 400° C. for 24 hours and, after calcination, stored under an inert atmosphere, nitrogen, until used. All preparations and handling were carried out under a nitrogen atmosphere at room temperature. The calcined alumina was transferred into a pressure equalizing addition funnel (a column), and to this alumina was added 56 ml of TIBAL in heptane solution. The system was allowd to stand for 1 hour after which the remaining TIBAL in heptane solution was drained from the column. Then 50 ml of heptane was added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 7.1 to 8.0 wt. % isobutane were obtained.

EXAMPLE 8

The following materials were utilized in the preparation of the purifying agent:

20 g of alumina, formed into spheres;

60 ml of triethyl aluminum (TEAL ) in heptane, (25 wt. %) solution; and 150 ml of heptane distilled over calcium hydride and stored under nitrogen.

The alumina was first calcined in a flow of nitrogen at 400° C. for 24 hours and then stored under an inert atmosphere, nitrogen, until used. All preparations and handling were carried out under a nitrogen atmosphere at room temperature. The calcined alumina was transferred into a pressure equalizing addition funnel (a column) and to this alumina was added 30 ml of TEAL in heptane solution. The system was allowed to stand for 1 hour and the TEAL in heptane solution was then drained. To the wet alumina was added an additional 30 ml of TEAL in heptane solution and the system was allowed to stand for one hour after which time the remaining TEAL in heptane solution was drained from the column. Then 50 ml of heptane was added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 5.9 to 6.2 wt. % ethane were obtained. EXAMPLE 9

The following materials were utilized in the preparation of the purifying agent:

20 g of alumina, formed into spheres;

30 ml of triethyl aluminum (TEAL) in heptane, (5 wt. %) solution;

30 ml of triethyl aluminum (TEAL) in heptane, (25 wt. %) solution; and 150 ml of heptane distilled over calcium hydride and stored under nitrogen.

The alumina was first calcined in a flow of nitrogen at 400° C. for 24 hours and then stored under an inert atmosphere, nitrogen, until used. All preparations and handling were carried out under a nitrogen atmosphere at room temperature. The calcined alumina was transferred into a presssure equalizing addition funnel (a column) and to this alumina was added 30 ml of TEAL in heptane solution, 5 wt. % concentration. The system was allowed to stand for 30 minutes, and the TEAL in heptane solution was then drained. To the wet alumina was added 30 ml of TEAL in heptane solution, 25 wt. % concentration, and the system was allowed to stand for one hour after which time the remaining TEAL in heptane solution was drained from the column. Then 50 ml of heptane was added and allowed to stand for 10 minutes after which time the heptane was drained. An additional 50 ml of heptane was then added and allowed to stand for 10 minutes followed by draining. A third portion of 50 ml of heptane was added, allowed to stand for 10 minutes and then drained. The resulting wet material was then dried under vacuum at room temperature. Loadings of 4.7–4.9 wt. % ethane were obtained.

EXAMPLE 10

The following materials were utilized in the preparation of the purifying agent as detailed:

20 g of silica formed into spheres obtained from the PQ Corporation of Pennsylvania, Code #CD 110B, a developmental product;

30 ml of triethyl aluminum (TEAL) in heptane (25 wt. %) solution; and 200 ml of heptane distilled over calcium hydride and stored under nitrogen.

The silica was first calcined in a flow of nitrogen, at 400° for 24 hours and then stored under an inert atmosphere, nitrogen, until used. All preparations and handling were carried out under a nitrogen atmosphere at room temperature. The calcined silica was transferred into a 3 necked round bottom flask equipped with a means of stirring. To the silica was added 50 ml of heptane and the silica/heptane mixture was stirred. To this mixture was added 30 ml of TEAL in heptane solution and the system was stirred for four hours. After four hours the remaining TEAL in heptane solution was decanted, a 50 ml portion of heptane was added and the system was stirred for 10 minutes. This heptane was decanted and a fresh 50 ml portion of heptane added, followed by stirring for 10 minutes and decanting off the heptane. A final 50 ml portion of heptane was added, the system was stirred for 10 minutes and then the heptane was decanted. This resulting wet material was then dried under vacuum at room temperature. Loadings of TEAL as measured by weight percent ethane evolved on hydrolysis were in the range of 1.6 to 2.4 wt. % ethane. It should be noted that the presence or absence of surface hydroxyl groups on the above silica was not determined prior to use. EXAMPLE 11

Pretreatment conditions, residence time, type of alumina support material, stirring reaction time, temperature, and TEAL concentrations in heptane were varied to determine their effects on loading of the organometallic compound prepared by the process disclosed in Example 3. The data contained below in Tables I, II and III give the results.

All samples for Tables I, II and III were prepared using 20 g of Rhone Poulenc's (SCM-250A) alumina calcined in flowing nitrogen at 3000° C. for 24 hours. The TEAL to heptane ratio was calculated assuming all TEAL solutions were 25.0 wt. % in heptane, i.e., 21.35 volume % TEAL.

TABLE I

Effect of Reaction Time and TEAL Concentration on Loading of Alumina with TEAL at Room Temperature

| Sample No. | Heptane (ml) | 25% TEAL Solution (ml) | TEAL to Heptane Vol. Ratio | Reaction Time (hrs.) | Ethane (wt. %) |
|---|---|---|---|---|---|
| 1 | 50 | 30 | 0.087 | 1 | 4.6 |
| 2 | 50 | 30 | 0.087 | 2 | 5.5 |
| 3 | 50 | 30 | 0.087 | 4 | 5.7 |
| 4 | 50 | 30 | 0.087 | 4 | 5.3 |
| 5 | 50 | 60 | 0.132 | 1 | 4.6 |
| 6 | 50 | 60 | 0.132 | 2 | 6.0 |
| 7 | 50 | 60 | 0.132 | 2 | 6.0 |
| 8 | 50 | 60 | 0.132 | 4 | 8.0 |
| 9 | 50 | 60 | 0.132 | 4 | 6.8 |
| 10 | 50 | 60 | 0.132 | 6 | 6.9 |
| 11 | 30 | 36 | 0.132 | 2 | 4.9 |
| 12 | 30 | 36 | 0.132 | 2 | 6.6 |
| 13 | 25 | 30 | 0.132 | 2 | 6.2 |
| 14 | 30 | 36 | 0.132 | 4 | 6.5 |
| 15 | 30 | 54 | 0.159 | 2 | 5.9 |
| 16 | 30 | 54 | 0.159 | 2 | 6.0 |

TABLE II

Effect of Reaction Time and TEAL Concentration on Loading of Alumina with TEAL at 80° C.

| Sample No. | Heptane (ml) | 25% TEAL Solution (ml) | TEAL to Heptane Vol. Ratio | Reaction Time (hrs.) | Ethane (wt. %) |
|---|---|---|---|---|---|
| 17 | 50 | 30 | 0.087 | 2 | 5.5 |
| 18 | 50 | 30 | 0.087 | 2 | 5.8 |
| 19 | 50 | 30 | 0.087 | 2 | 5.5 |
| 20 | 50 | 30 | 0.087 | 4 | 6.1 |
| 21 | 50 | 30 | 0.087 | 4 | 6.2 |
| 22 | 50 | 60 | 0.132 | 2 | 6.5 |
| 23 | 50 | 60 | 0.132 | 2 | 6.8 |
| 24 | 50 | 60 | 0.132 | 4 | 7.0 |
| 25 | 50 | 60 | 0.132 | 4 | 7.0 |
| 26 | 30 | 36 | 0.132 | 4 | 7.2 |

TABLE III

Effect of Reaction Time and TEAL Concentration on Loading of Alumina with TEAL at Reflux, 98° C.

| Sample No. | Heptane (ml) | 25% TEAL Solution (ml) | TEAL to Heptane Vol. Ratio | Reaction Time (hrs.) | Ethane (wt. %) |
|---|---|---|---|---|---|
| 27 | 50 | 60 | 0.132 | 2 | 7.9 |
| 28 | 50 | 60 | 0.132 | 2 | 6.8 |
| 29 | 50 | 60 | 0.132 | 4 | 6.8 |
| 30 | 30 | 36 | 0.132 | 0.75 | 4.9 |
| 31 | 30 | 36 | 0.132 | 1.5 | 6.8 |
| 32 | 30 | 36 | 0.132 | 2 | 7.6 |
| 33 | 30 | 36 | 0.132 | 2 | 6.9 |
| 34 | 30 | 36 | 0.132 | 3 | 6.0 |
| 35 | 30 | 36 | 0.132 | 4 | 6.2 |
| 36 | 30 | 36 | 0.132 | 6 | 6.8 |
| 37 | 30 | 54 | 0.159 | 2 | 7.6 |
| 38 | 50 | 90 | 0.191 | 2 | 8.0 |
| 39 | 50 | 90 | 0.191 | 4 | 7.7 |

At room temperature the highest loading of TEAL on alumina was obtained with a 4 hr. reaction time and a 0.132 TEAL to heptane ratio. At 80° C. the highest loading is again at a 0.132 TEAL to heptane ratio but a reaction time of 2 hrs. gives very similar results to that of 4 hrs. At reflux temperature a reaction time of 2 hrs. or greater gives equivalent loadings at a TEAL to heptane ratio of 0.132, however, addition of more TEAL increases this loading slightly. Thus, equivalent loadings can be obtained using a room temperature reaction for 4 hrs. for 80° C. and 98° C. for 2 hrs.

Use of the supported organometallic compound for purifying fluid is within the knowledge of one having skill in the art. The purifying agent in the practice of the invention is contacted with the fluid to be purified in an amount and for a sufficient time necessary to remove impurities therefrom. Amounts of the purifying agent necessary to purify a particular fluid will of course vary with the amount of fluid being treated and the amount and kinds of impurities present. This is also true for the contact time necessary to obtain the removal of impurities. No undue experimentation is required to ascertain the amount and contact time necessary to purify materials within the scope described.

The following Examples exemplify the use of the purifying agent. In the examples, reference to large scale comprises a variation in the preparation of the previous Examples wherein 700 grams of alumina is treated with from about 800 to about 1200 ml of 25 wt. % TEAL solution in about 500 ml of heptane and then washed with a total of 1500 ml of heptane. The experimental equipment and procedure described below were utilized in the following examples:

CDS REACTOR

The CDS reactor, Model 810 micro pilot plant reaction system, can be obtained commercially from Chemical Data Systems. The reactor was modified by addition of a valve in order to allow loading and unloading the samples under an inert atmosphere. The reactor allows gases to be passed over the sample with a downward flow and the effluent gas from the reactor is sampled to a gas chromatograph via an automated sampling valve. The reactor was normally packed with a 10.0 g sample under nitrogen by use of a dry-box. Testing was carried out at 1 atmosphere pressure and 60° C. with a flow of gas of 72 cm$^3$/min.

SLURRY POLYMERIZATION REACTOR TESTING

In order to test the efficacy of the prepared TEAL on alumina or TMAL on alumina samples, for propylene purification under pressure (90 psig, 721.8 kPa), modifications were made to the piping in a slurry reactor facility such that the feed propylene passed over molecular sieves and then through a one liter stainless steel cylinder located in each reactor bay which could be packed with TEAL on alumina, TMAL on alumina, alumina alone, or molecular sieves. The stainless steel cylinders were packed with approximately 700 g of sample for each bay. The polymerization conditions employed for the Stauffer 1.13 olefin polymerization catalyst (a catalyst prepared in accordance with the invention disclosed in U.S. Pat. No. 4,124,530 without an agglomeration control additive) were that Bays 1 and 4, were at a temperature of 70° C., and a propylene pressure of 90 psig (721.8 kPa) for a time of 3 hours, using 400 mg of 1.13 catalyst and a 4:1 molar ratio of total Al:Ti. For a magnesium chloride-supported titanium catalyst (a catalyst prepared in accordance with U.S. Pat. No. 4,450,242), the conditions used in reactor Bays 2 and 3, were a temperature of 65° C., a pressure of 90 psig (721.8 kPa) for a time of 2 hours with 500 mg of supported catalyst and a 4:1 molar ratio of TEAL co-catalyst:electron donor (methyl-p-toluate). The approximate contact time for the propylene with the TEAL on alumina sample in the feed line was 3 to 30 seconds calculated using linear velocity. Comparisons of the polymerization activity and isotactic index (II) for the polypropylene produced were made with and without the TEAL on alumina and TMAL on alumina samples in the feed propylene line. These results are shown in Tables IV, V, VI and VII which follow.

EXAMPLE 12

Removal of Oxygenates for Dicyclopentadiene

All preparations and handling were carried out in the absence of air under nitrogen at room temperature. A 50 g amount of TEAL on alumina prepared according to Example 3 (large scale) was placed in a pressure equalizing funnel and to this was added 50 ml of a 50:50 mixture of heptane (dried over calcium hydride) and dicyclopentadiene. This mixture was allowed to contact the TEAL on alumina for 2 hrs. and 40 minutes after which time it was drained from the funnel and collected. A second portion of 50 ml of the 50:50 mixture of heptane and dicyclopentadiene was added to the addition funnel and allowed to contact the TEAL on alumina for 2 hrs. and 40 minutes after which time it was drained and collected. The collected portions of the 50:50 mixture of heptane and dicyclopentadiene are termed the "treated material".

Analysis of the initial untreated material was 400 ppm oxygenates.

Analysis of the treated material was <5 ppm oxygenates.

EXAMPLE 13

Removal of Sulfur Containing Compounds from Kerosene Solvent

All preparations and handling were carried out in the absence of air under nitrogen at room temperature. A 50 g amount of TEAL on alumina prepared in accordance with Example 3 (large scale) was placed in a pressure equalizing funnel and to this was added 50 ml of the kerosene solvent. The solvent was allowed to contact the TEAL on alumina for 2 hrs. and 40 minutes after which time it was drained and collected. A second portion of 50 ml kerosene was added to the TEAL on alumina and allowed to contact it for 2 hrs. and 40 mins. This kerosene was also drained and collected. The collected kerosene is termed the "treated material".

Analysis of the initial untreated material gave 69 ppm total sulfur.

Analyzing the treated material gave 34 ppm total sulfur.

EXAMPLE 14

Propylene Purification

A 750 gram amount of TEAL on $Al_2O_3$ prepared in accordance with Example 3 (large scale) was loaded into a stainless steel cylinder equipped with valves at both ends, under an inert atmosphere, and then installed into a propylene feed line to the slurry polymerization reactors. The efficacy of the propylene to achieve polymerization using both the previously described 1.13 catalyst and the magnesium chloride-supported titanium catalyst was evaluated. The most obvious differences are seen in Tables IV and V using propylene obtained from Northern Petrochemical Co. of Omaha, Nebr. and Scientific Gas Products Co. of South Plainfield, N.J. Subsequent analysis of the Northern Petrochemical tank of propylene is listed below.

| Northern Petrochemical Propylene | |
|---|---|
| Impurity | Amount |
| CO | not detected |
| $CO_2$ | 0.05 ppm |
| Methane | not detected |
| Ethylene | 0.02 ppm |
| Ethane | 0.3 ppm |
| Water | not detected |
| Oxygen | approx. 150 ppm |

The purification system was tested in the propylene feed lines to the slurry reactors used for propylene polymerization. Catalyst activities and isotactic indices (II) were obtained using molecular sieves (baseline), molecular sieves and TEAL on alumina (purification) and using molecular sieves plus alumina (alumina). Two sources of propylene were used, as indicated above, the one from Scientific Gas Products Co. (A) and the other from Northern Petrochemical Co. (B).

The catalysts utilized were those previously referred to as the 1.13 catalyst and the magnesium chloride-supported titanium catalyst (designated high mileage catalyst or "HM catalyst"). The contact time of the propylene fed stream with the purification agent was two to twenty seconds.

The results obtained are shown in Tables IV and V which follow.

TABLE IV

| PROPYLENE FROM SOURCE A* | | | | |
|---|---|---|---|---|
| | Baseline | | Purification | |
| | Activity | II | Activity | II |
| Bay 1 - 1.13 catalyst | | | | |
| mean | 936 | 94 | 927 | 94.1 |
| Std. Dev. | 37 | 0.6 | 26 | 0.9 |
| Bay 2 - HM catalyst | | | | |
| mean | 7865 | 84.3 | 7252** | 87.4** |
| Std. Dev. | 263 | 1.1 | — | — |
| Bay 3 - HM catalyst | | | | |
| mean | 7354 | 85.6 | 7253 | 88.8 |
| Std. Dev. | 233 | 1.0 | 260 | 0.9 |
| Bay 4 - 1.13 catalyst | | | | |
| mean | 839 | 96.8 | 892 | 95.9 |
| Std. Dev. | 139 | 0.2 | 53 | 0.6 |

*Average of 5 runs except where noted
**Only 2 runs

TABLE V

| PROPYLENE FROM SOURCE B* | | | | | | |
|---|---|---|---|---|---|---|
| | Baseline | | Alumina | | Purification | |
| | Activity | II | Activity | II | Activity | II |
| Bay 1 - 1.13 catalyst | | | | | | |
| Mean | 918 | 94.3 | — | — | 925 | 94.2 |
| Std. Dev. | 19 | 0.7 | — | — | 23 | 1.1 |
| Bay 2 - HM catalyst | | | | | | |
| Mean | 5155 | 88.7 | 6448 | 87.0 | 7648 | 85.7 |
| Std. Dev. | 680 | 1.8 | 764 | 1.3 | 646 | 1.5 |
| Bay 3 - HM catalyst | | | | | | |
| Mean | 6310 | 87.4 | 6618 | 85.6 | 7533 | 85.2 |
| Std. Dev. | 714 | 1.6 | 687 | 1.6 | 520 | 1.6 |
| Bay 4 - 1.13 catalyst | | | | | | |
| Mean | 889 | 94.5 | — | — | 933 | 95.4 |
| Std. Dev. | 44 | 0.8 | — | — | 23 | 0.4 |

*Average of 4 or 5 runs

The results obtained for Source A (polymerization grade propylene) disclosed no significant differences with respect to activity or II for the 1.13 catalyst or the HM catalyst which is possibly due to the high purity of the propylene used, whereas the results for source B shows a significant improvement (average 30%) in the activity of the HM catalyst and some increase for the 1.13 catalyst.

EXAMPLE 15

A second tank of propylene was obtained from Northern Petrochemical Co. (B). The analysis of the propylene gave the following:

| Northern Petrochemical Tank 2 | |
|---|---|
| CO | Not detected |
| $CO_2$ | 0.2 ppm |
| Methane | Not detected |
| Ethylene | 0.4 ppm |
| Ethane | 1.8 ppm |
| Water | 150–250 ppm |
| Oxygen | approx. 300 ppm |

Following the procedure of Example 14, polymerization runs were conducted, the results of which are given in Table VI.

TABLE VI

| | Baseline (MS) | Alumina (MS + $Al_2O_3$) | Mole Sieves (MS + MS) | Purification (MS + TEAL on $Al_2O_3$) |
|---|---|---|---|---|
| Bay 1 - 1.13 catalyst | | | | |
| Activity | No Polymer | | | 944 |
| II | | — | — | 94.1 |
| No. Runs | 1 | | | 1 |
| Bay 2 - HM catalyst | | | | |
| Activity | No Polymer | No Polymer | 320 | 6195 |
| II | | | 92.4 | 88.0 |
| No. Runs | 2 | 1 | 1 | 1 |

MS = Molecular Sieves

As indicated in the Table VI, testing of this second tank of propylene under baseline conditions or with alumina in line gave no polymer; however, with the TEAL on alumina system in line, a normal activity was obtained for both the 1.13 and HM catalysts. When additional molecular sieves were used in the feed line for the HM catalyst, an extremely low activity was obtained implying that one of the additional impurities present in the second tank of propylene was water.

EXAMPLE 16

A 750 gram amount of TEAL on alumina prepared in accordance with Example 3 (large scale) and TMAL on alumina prepared in accordance with Example 5 (large scale) were loaded into two separate stainless steel cylinders equipped with valves at both ends under an inert atmosphere. Each was separately tested for removal of impurities in propylene in the slurry reactor feed lines.

Analysis of the propylene before and after treatment with TEAL on alumina and TMAL on alumina was carried out, see below:

| | Impurities (concentration in ppm) | | | | |
|---|---|---|---|---|---|
| | CO | $CO_2$ | Ethylene | Ethane | Methane* |
| Propylene alone | 0.08 | 0.9 | 3.6 | 39 | 5 |
| Propylene treated with TEAL on alumina | ND | 0.1 | 17 | 110 | 6 |
| Propylene treated with TMAL on $Al_2O_3$ | 0.1 | 0.2 | 24 | 49 | 69 |

*Methane value is estimated, ND - not detected

In addition, the following compounds were analyzed and not detected in the propylene alone or after treatment, acetylene, allene, methyl acetylene and $C_4$ hydrocarbons.

EXAMPLE 17

The TEAL on alumina and TMAL on alumina-treated propylene were used in the polymerization of propylene using the HM catalyst previously mentioned (U.S. Pat. No. 4,450,242). The results are shown in Table VII. The polymerization runs were carried out as indicated at 65° C. at a pressure of 90 psig (721.8 kPa) for 2 hours using 50 mg of catalyst and using a 4:1 molar ratio of TEAL to electron donor (methyl-p-toluate). "Baseline" indicates use of molecular sieves and BASF catalyst (CuO on alumina) to remove impurities whereas "TEAL on alumina" and "TMAL on alumina" indicates the additional use of these materials to remove impurities.

The TEAL on alumina and TMAL on alumina both improve the activity of the catalyst by 7–10% in comparison with the baseline runs.

TABLE VII

| | Baseline | | TEAL on Alumina | | TMAL on Alumina | |
|---|---|---|---|---|---|---|
| | Activity | II | Activity | II | Activity | II |
| | 7708 | 87.6 | 8320 | 90.7 | 8463 | 88.2 |
| | 8325 | 86.5 | 7925 | 89.9 | 8570 | 87.5 |
| | 7455 | 87.7 | 8778 | 87.9 | 7938 | 88.9 |
| | 7503 | 91.2 | 8749 | 86.7 | 8590 | 88.1 |
| | | | | 86.4 | 7868 | 89.9 |
| Mean | 7748 | 88.2 | 8499 | 88.3 | 8286 | 88.5 |
| Std. Dev. | 400 | 2.0 | 371 | 1.9 | 354 | 0.9 |

EXAMPLE 18

Figure 1:
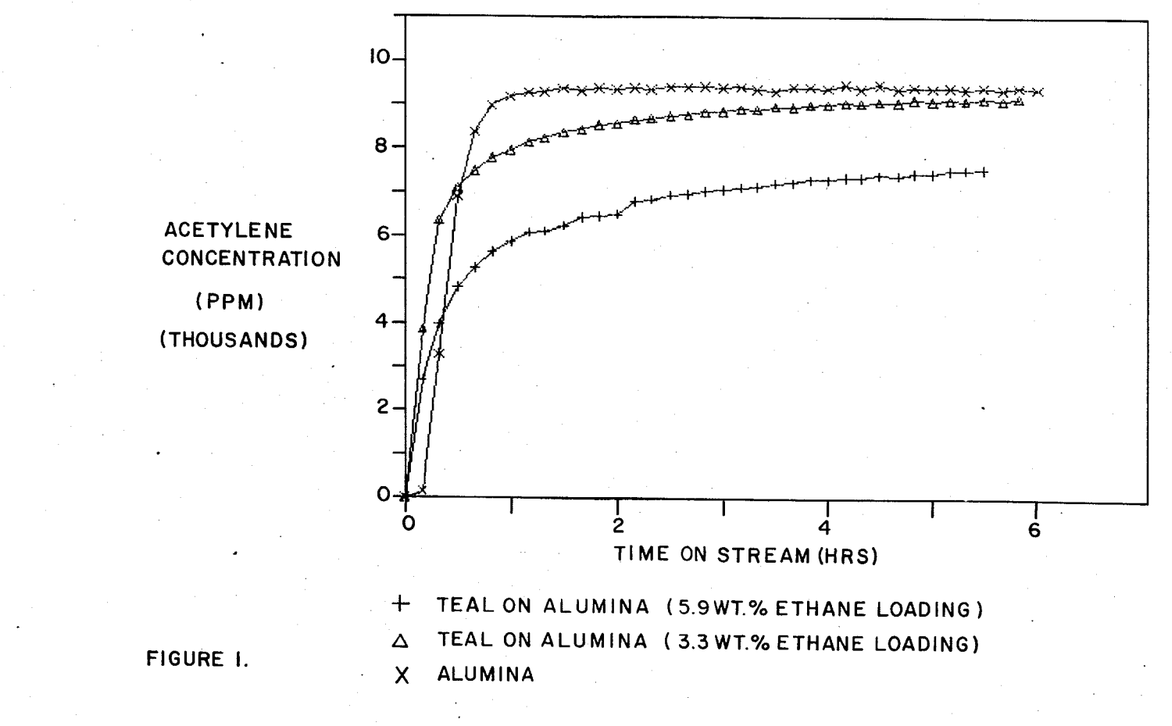
FIG. 1 is a graphical representation of the effectiveness of the purifying agent of this invention on the removal of acetylene from helium.

Samples comprising 10.0 g of TEAL on $Al_2O_3$ prepared in accordance with Examples 1 and 2, or alumina alone were loaded into the CDS reactor in an inert atmosphere. Over each sample of material in the reactor was passed 0.98% acetylene in helium gas at a flow rate of 72 cm$^3$/min at atmosphere pressure and 60° C. The concentration of acetylene was monitored in the effluent stream by gas chromatography. FIG. 1 shows the acetylene concentration versus the time that the system was on-stream.

The TEAL on alumina prepared in accordance with Example 1 had a loading of 5.9 wt. % ethane and that made in accordance with Example 2 had a loading of 3.3 wt % ethane. It can be seen from FIG. 1 that the sample with a 5.9 wt. % ethane loading was more effective at removing acetylene than the sample with the 3.3 wt. % ethane loading. Both, however, are shown to be more effective than alumina alone.

EXAMPLE 19

The material purified in the following Example is compressed helium gas containing: 18 ppm carbon monoxide; 16 ppm carbon dioxide; 19 ppm acetylene; 19 ppm ethylene; 18 ppm ethane; 18 ppm methyl acetylene; 12 ppm allene; 0.994% propylene, and the rest being helium.

The purifying agent prepared in accordance with Example 1 TEAL on alumina (large scale), Example 5 TMAL on alumina (large scale), Example 7 TIBAL on alumina, and alumina alone were assessed in purifying the compressed helium.

A 10.0 g amount of the alumina and respectively each of TEAL on $Al_2O_3$, TMAL on $Al_2O_3$ and TIBAL on $Al_2O_3$ were individually tested by being loaded into the CDS reactor in an inert atmosphere. The compressed gas detailed above was passed over the bed of material in each run at a flow rate of 72 cm$^3$/min at atmospheric pressure and 50° C. The effluent gas was monitored using a specialized gas chromatograph, Carle, Series 500, calibrated to monitor the levels of the impurities CO, $CO_2$, acetylene, methyl acetylene and allene.

Figure 2A:
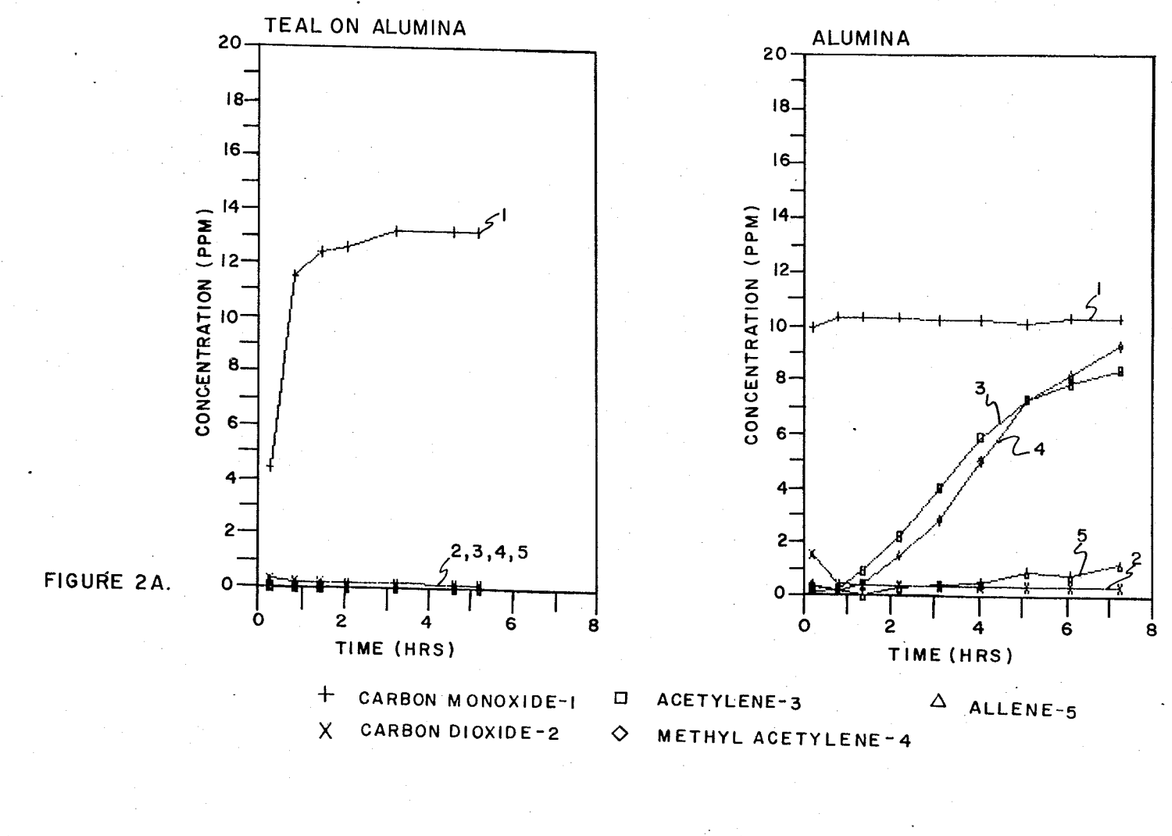
FIGS. 2A-2B are graphical representations of the varying effectiveness of the purifying agents of this invention compared to alumina in removing various impurities from compressed helium gas.
Figure 2B:
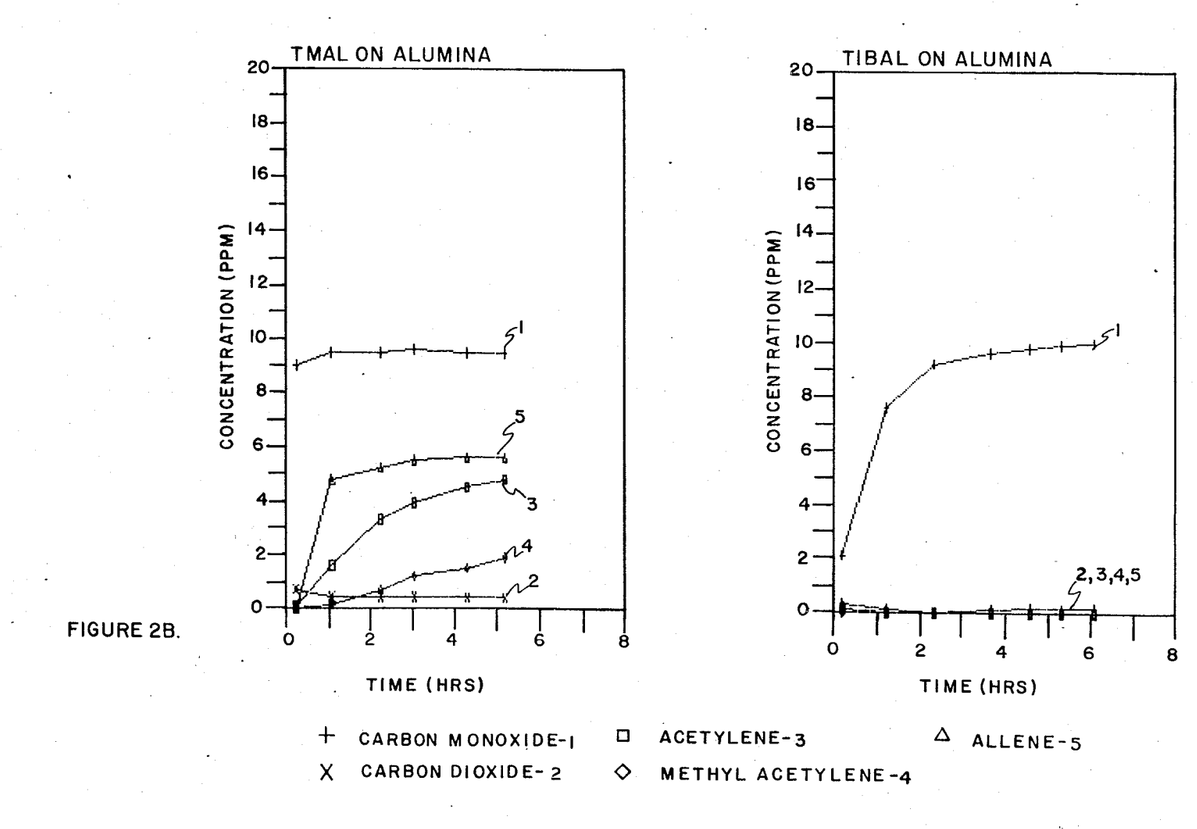

Plots of the concentration of these impurities versus time on stream are shown in FIGS. 2A-2B. It can be seen that the TEAL on alumina and TIBAL on alumina remove acetylene and methyl acetylene to below the detection limit for the five hours monitored. In addition, the TEAL on alumina removes allene to below the detection limit. The TIBAL on alumina removes allene to a level of less than 0.2 ppm throughout the run. All samples studied remove $CO_2$ to less than 0.5 ppm and none of the samples are effective at removing CO significantly. The TMAL on alumina and alumina alone do not effectively remove the other impurities studied.

EXAMPLE 20

Figure 3:
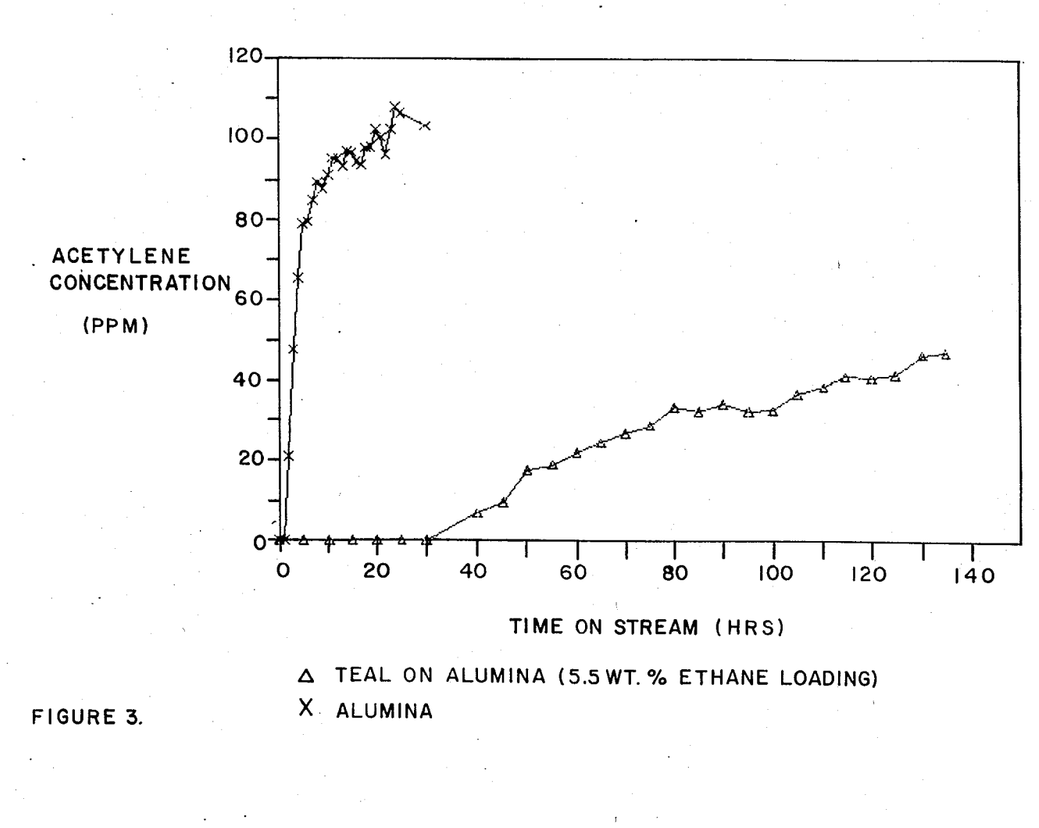
FIG. 3 shows graphically the removal of acetylene from helium using triethyl aluminum on alumina as compared with alumina.

A 10.0 g sample of TEAL on alumina prepared as in Example 1 with a loading of 5.5 wt. % ethane, was compared to a 10.0 g. sample of alumina alone for removal of 108 ppm acetylene in helium using the CDS reactor. The 108 ppm of acetylene in helium was passed over the samples at a flow rate of 72 cm$^3$/min at atmospheric pressure and 50° C. The effluent gas was monitored by gas chromatography. FIG. 3 shows a plot of acetylene concentration versus time on stream. It can be seen from the graph that the TEAL on alumina effectively removes the 108 ppm of acetylene from the feed stream for 40 hours whereas the alumina only functions for approximately 1 hour.

EXAMPLE 21

The following materials were utilized in a purification process as disclosed herein:

13 g of TEAL on alumina prepared according to Example 3, crushed into a powder in an inert atmosphere; and 32 g alpha-pinene containing 300 ppm sulfur impurities.

The powdered TEAL on alumina was packed in a column 8" long by ¾" diameter and the 32 g of alpha-pinene was allowed to flow through the packed bed at an average flow rate of 0.133 g/min. All operations were carried out under nitrogen in the absence of air. Analysis of the treated alpha-pinene gave a total sulfur level of 7 ppm, i.e. removal of 293 ppm of sulfur-containing impurities.

What is claimed is:

1. A purifying agent for fluids comprising a granular metal oxide-supported organometallic compound, wherein the metal oxide has a particle size of from about 0.16 cm to about 1.3 cm.

2. The purifying agent of claim 1 wherein the support is a hydroxyl ion containing metal oxide.

3. The purifying agent of claim 2 wherein the metal oxide comprises at least one oxide of a Group II to Group IV metal.

4. The purifying agent of claim 3 wherein the metal oxide is alumina.

5. The purifying agent of claim 1 wherein the organometallic compound comprises at least one $C_1$ to $C_8$ alkyl.

6. The purifying agent of claim 5 wherein the organometallic compound comprises at least one Group II to Group IV metal.

7. The purifying agent of claim 1 wherein the organometallic compound is a trialkyl aluminum.

8. The purifying agent of claim 7 wherein the trialkyl aluminum is triethyl aluminum.

9. The purifying agent of claim 7 wherein the trialkyl aluminum is trimethyl aluminum.

10. The purifying agent of claim 7 wherein the trialkyl aluminum is triisobutyl aluminum.

11. A process for preparing a supported organometallic compound comprising reacting a calcined granular hydroxyl ion-containing metal oxide, having a particle size of from about 0.16 cm to about 1.3 cm, with an organometallic compound to form a supported material.

12. The process of claim 11 wherein a powdered hydroxyl ion-containing material is used to form the supported organometallic compound which is thereafter shaped to form a granular material supported compound.

13. The process of claim 11 wherein the calcining is conducted under an inert atmosphere.

14. The process of claim 11 wherein the calcining is conducted in air.

15. The process of claim 11 wherein the hydroxyl ion containing metal oxide comprises at least one oxide of a Group II to Group IV metal.

16. The process of claim 15 wherein the metal oxide is alumina.

17. The process of claim 11 wherein the organometallic compound comprises at least one Group II to Group IV metal.

18. The process of claim 11 wherein the organometallic compound is a trialkyl aluminum compound.

19. The process of claim 18 wherein the trialkyl aluminum compound is triethyl aluminum.

20. The process of claim 18 wherein the trialkyl aluminum compound is trimethyl aluminum.

21. The process of claim 18 wherein the trialkyl aluminum is triisobutyl aluminum.

22. The process of claim 11 wherein the reaction of the metal oxide support and the organometallic compound is conducted under an inert atmosphere.

23. The process of claim 11 wherein the organometallic compound is reacted neat with the metal oxide.

24. The process of claim 11 wherein the organometallic compound is mixed with a solvent prior to reaction with the metal oxide support.

25. The process of claim 24 wherein the solvent is a hydrocarbon solvent.

26. The process of claim 25 wherein the hydrocarbon solvent is a saturated hydrocarbon.

27. The process of claim 25 wherein the hydrocarbon solvent is an aromatic hydrocarbon.

28. The process of claim 25 wherein the solvent has a boiling point of less than about 150° C.

29. A process for preparing a supported organometallic compound comprising reacting a calcined granular hydroxyl ion-containing metal oxide, having a particle size of from about 0.16 cm to about 1.3 cm, with an organometallic compound in the presence of a solvent to form a supported material.

30. The process of claim 29 further comprising washing and drying the supported material.

31. The process of claim 11 wherein the metal oxide is calcined at a temperature of from about 150° C. to about 800° C.

32. The process of claim 11 wherein the molar ratio of organometallic compound to support is from about 0.05:1 to about 5:1.

33. The process of claim 32 wherein the preferred molar ratio of organometallic compound to support is from about 0.2:1 to about 0.5:1.

34. A purifying agent for fluids produced by the process comprising reacting a granular hydroxyl ion-containing metal oxide with an organometallic compound to produce a granular metal oxide supported organometallic compound, said metal oxide having a particle size of from about 0.16 cm to about 1.3 cm.

35. The process of claim 11 further comprising washing and drying the supported material.

36. The purifying agent of claim 1 wherein the molar raio of organometallic compound to support is from about 0.05:1 to about 5:1.

37. The purifying agent of claim 36 wherein the molar ratio of organometallic compound to support is from 0.2:1 to about 0.5:1.

* * * * *

UNITED STATES PATENT AND TRADEMARK OFFICE
CERTIFICATE OF CORRECTION

PATENT NO. : 4,614,729

DATED : September 30, 1986

INVENTOR(S) : Janet E. Crawford et al.

It is certified that error appears in the above—identified patent and that said Letters Patent is hereby corrected as shown below:

Col. 2, line 18-19, "apparanently" should be --apparently--.
Col. 2, line 12, "heterogenous" should be --heterogeneous--.
Col. 2, line 19, "are" should be inserted between "incorrectly)" and "represented".
Col. 3, line 15, "system" should be --stream--.
Col. 4, line 56, "174 inch" should be --1/4 inch--.
Col. 7, line 52, delete "capable".
Col. 10, line 22, after "necked" insert --round--.
Col. 11, line 12, "allowd" should be --allowed--.
Col. 12, line 32, "400°" should be --400°C--.
Col. 12, line 65, "3000°C" should be --300°C--.
Col. 15, line 5, "for" should be --from--.
Col. 15, line 46, "69 ppm" should be --68 ppm--.
Col. 16, line 24, "time" should be --times--.
Col. 22, line 22, "raio" should be --ratio--.
Cols. 11&12, lines 54&55 respectively, EXAMPLE 9 and EXAMPLE 11 are not centered.

Signed and Sealed this

Seventeenth Day of February, 1987

*Attest:*

DONALD J. QUIGG

*Attesting Officer*  *Commissioner of Patents and Trademarks*